United States Patent [19]
Fergason et al.

[11] Patent Number: 5,749,096
[45] Date of Patent: May 12, 1998

[54] HELMET WITH HIGH PERFORMANCE HEAD AND FACE PROTECTION UTILIZING COMPLEMENTARY MATERIALS

[75] Inventors: Jeffrey K. Fergason, Menlo Park, Calif.; David Fry, Holland, Mich.; Stephen M. Brunnell, Palo Alto, Calif.

[73] Assignee: Ilixco, Inc., Menlo Park, Calif.

[21] Appl. No.: 270,633

[22] Filed: Jul. 1, 1994

[51] Int. Cl.⁶ .................................................. A42B 3/00
[52] U.S. Cl. ............................... 2/8; 2/410; 2/412
[58] Field of Search ............................ 2/7, 8, 9, 412, 2/5, 2.5, 425, 410, 411

[56] References Cited

U.S. PATENT DOCUMENTS

| | | | |
|---|---|---|---|
| 3,001,900 | 9/1961 | Frieder et al. | 2/2.5 |
| 3,868,726 | 3/1975 | LaMarre et al. | 2/8 |
| 3,983,306 | 9/1976 | Nielinger et al. | 428/474 |
| 4,075,717 | 2/1978 | Lemelson | 2/412 |
| 4,300,242 | 11/1981 | Nava et al. | |
| 4,391,924 | 7/1983 | Uram, Jr. | 521/178 |
| 4,466,138 | 8/1984 | Gessalin | 2/410 |
| 4,473,208 | 9/1984 | Nava | |
| 4,656,674 | 4/1987 | Medwell | |
| 4,693,678 | 9/1987 | Von Volkli | |
| 4,728,173 | 3/1988 | Toth | 350/332 |
| 4,734,940 | 4/1988 | Galet et al. | 2/5 |
| 4,845,786 | 7/1989 | Chiarella | |
| 4,853,973 | 8/1989 | Boochard | 2/8 |
| 4,908,877 | 3/1990 | White | |
| 4,950,445 | 8/1990 | Salce et al. | |
| 4,953,234 | 9/1990 | Li et al. | 2/412 |
| 5,018,220 | 5/1991 | Lane et al. | 2/5 |
| 5,062,156 | 11/1991 | Siegal | |
| 5,074,647 | 12/1991 | Fergason et al. | 359/63 |
| 5,119,516 | 6/1992 | Broersma | 2/425 |
| 5,208,688 | 5/1993 | Fergason et al. | 359/53 |
| 5,224,219 | 7/1993 | Edwards et al. | 2/8 |
| 5,248,880 | 9/1993 | Fergason | 250/205 |
| 5,252,817 | 10/1993 | Fergason et al. | 250/205 |
| 5,349,893 | 9/1994 | Dunn | 2/2.5 |
| 5,421,035 | 6/1995 | Klose et al. | 2/425 |
| 5,477,563 | 12/1995 | Gentes et al. | 2/425 |
| 5,522,198 | 6/1996 | Byer et al. | |
| 5,548,848 | 8/1996 | Huybrechts | 2/425 |

FOREIGN PATENT DOCUMENTS

WO9114809  12/1990  WIPO.

*Primary Examiner*—Michael A. Neas
*Attorney, Agent, or Firm*—Renner, Otto, Boisselle & Sklar

[57] ABSTRACT

A structure formed of a composite material and a support material, the support material being integrally coupled to the composite material by an insert molding process to form an integral structure, and protective head gear, such as a welding helmet, welding shield, hard hat, etc. using such structure. A method for making a structure using sheet-like composite material includes adhering to the composite material a relatively rigid support member or frame by insert molding directly to the composite material.

41 Claims, 4 Drawing Sheets

HELMET WITH HIGH PERFORMANCE HEAD AND FACE PROTECTION UTILIZING COMPLEMENTARY MATERIALS

TECHNICAL FIELD

The present invention relates generally, as is indicated, to structures including a composite material and a support material combined in an integral fashion, and, more particularly, to head and face protection devices utilizing complementary composite and thermoplastic materials. Exemplary head and face protection devices include welder's shields and helmets and hard hats. The invention also relates generally to use of composite panels insert molded with a thermoplastic frame to form an integral structure.

BACKGROUND

Welders and others wear welding helmets, hard hats, face shielding devices, etc., to protect themselves from strong ultraviolet, visible and/or infrared light rays that are emitted from a welding arc. Welding helmets also provide a protective barrier between the welder and the welding arc fumes, heat, hot metal spatter, sparks, and possibly other flying debris.

An example of a welding helmet includes an outside shell with a viewing port, a mounting head band, and means for mounting a welding lens in the viewing port such as a viewing port filter plate retainer mechanism. The viewing port may include a darkened piece of glass, plastic or other material often referred to as a lens or as a welding lens, the object of which is to permit viewing of a welding operation while protecting the eyes of the welder from the ultraviolet, visible, and/or infrared light occurring during a welding operation. The lens also may be of the automatic type which darkens to block such light during welding and which lightens to transmit more light when welding is not occurring. Examples of such automatic welding lenses are disclosed in U.S. Pat. Nos. 5,208,688; 5,252,817; 5,248,880; and 5,074,647, the entire disclosures of which are hereby incorporated by reference. Other types of automatic welding lenses and fixed welding lenses may be used in welding helmets, as is known.

Various mounting headbands have been used to mount a welding helmet, hard hart, etc. on the head of a person. Modern headbands are adjustable to head size and typically are attached to and mounted on a welding helmet to permit relative pivoting movement to allow the helmet to be opened and/or to allow the helmet to be placed comfortably and securely on the head. A pivoting connection between the mounting headband and a welding face shield device, for example, also is used to enable tilting of the face shield between a down position in front of the face and an up position above the top of the head.

Welding helmet shells that are currently made are constructed primarily either of thermoplastic injection molded resins or blends; formed fiberglass or sheet resin materials; or pattern cut and fastened vulcanized fiberboard. These materials have been suitable for welding helmet construction because they offer adequate temperature and impact resistance, but they all are relatively heavy, usually weighing more than 0.5 pounds for the shell only. It would be desirable to reduce the weight of a welding helmet or like device. It also would be desirable to improve the resistance of a welding helmet to hot metal spatter and to sparks and to improve the durability and ability to withstand severe impacts.

Composite material as referred to herein means, for example, a material created from a fiber (or reinforcement) and an appropriate matrix material in order to provide, preferably to maximize, specific performance properties. The constituents do not dissolve or merge completely but retain their identities as they act in concert. Examples of composite material in the context of the present invention include woven fiber, such as that sold under the trademark Kevlar, embedded in a resin matrix, such as epoxy, polyimide, or polyester or other matrix materials. Such woven fiber and resin may form a single ply or a multiple ply (laminate) structure. Other exemplary composite materials are described below.

Although composite materials have a number of advantageous characteristics, such as light impermeability, especially when including a dye or other light blocking material, light weight, temperature resistance, and durability, other characteristics make them undesirable for use in welding helmets, hard hats, other face shielding devices, and other devices where structural integrity or continuity of shape are required. The cost to obtain the composite material thickness that is required for strength of the particular object is often prohibitive for their use.

It would be desirable to increase the utility of such composite materials, especially by making them easily used in devices which require such structural integrity. Examples of such devices may well be welding helmets, hard hats, face shielding devices, and/or other devices used for protective purposes, such as those mentioned above, and/or for other purposes.

Furthermore, it is difficult and sometimes not possible to form mechanical details in composite materials. An exemplary mechanical feature may be a support device, a support opening, and/or a threaded opening structure for connecting a mounting headband to a welding helmet shell. It would be desirable to provide in a device that uses composite material panels, sheets or the like, mechanical details for fastening, reinforcement, and/or other purposes.

Composite materials also tend to have relatively ragged or unsmooth edges, and various techniques have been used in the past to finish those edges to provide a smooth edge. Rough edges are undesirable because they can help cause the breakage of the composite panel upon side impact. It would be desirable to facilitate finishing such edges to provide smooth surfaces that are less likely to encounter breakage as well as to cause a potential hazard to the user.

SUMMARY

One aspect of the invention relates to a structure comprising a composite material and a support material, the support material being integrally coupled to the composite material to form an integral structure.

According to another aspect, a device for providing protection for a person includes a sheet-like composite material and a frame structure, the frame structure integrally bonded to the sheet-like composite material, and a mounting structure for positioning the device on a person.

A further aspect relates to a device for providing protection for a person including a sheet-like composite material and a frame structure, the frame structure integrally molded to the sheet-like composite material, and a mounting mechanism positioning device on a person.

An additional aspect relates to a light weight device for protecting a part of the body of a person including a plurality of relatively light weight panels of composite material and a frame structure for holding the panels in relatively fixed relation.

Still another aspect of the invention concerns protective gear for a person including a plurality of sheet-like panels of composite material and a frame insert molded directly to respective panels for holding the panels in relatively fixed position.

Yet a further aspect relates to a welding helmet including a plurality of panels of composite material, a frame structure of thermoplastic material securely adhered to the composite material by insert molding thereto, and a viewing port.

Yet an additional aspect relates to a method for making a structure using a sheet-like composite material including adhering to the composite material a relatively rigid support member.

Even another aspect of the invention relates to a method of making a device formed of a composite material and a frame including the steps of placing a sheet-like quantity of the composite material in a mold of a molding machine, placing material for forming the frame in the mold, and molding the frame directly to the composite material.

The foregoing and other objects, features, aspects and advantages of the invention will become more apparent as the following description proceeds. It will be appreciated that while an embodiment of the invention is described herein, the scope of the invention is to be determined by the claims and equivalents thereof. Also, although the invention is described with respect to a welding helmet, it will be appreciated that the concepts of the invention may be utilized in conjunction with other devices.

To the accomplishment of the foregoing and related ends, the invention, then, comprises the features hereinafter fully described in the specification and particularly pointed out in the claims, the following description and the annexed drawings setting forth in detail a certain illustrative embodiment of the invention, this being indicative, however, of but one of the various ways in which the principles of the invention may be suitably employed.

DESCRIPTION

Figure 1:
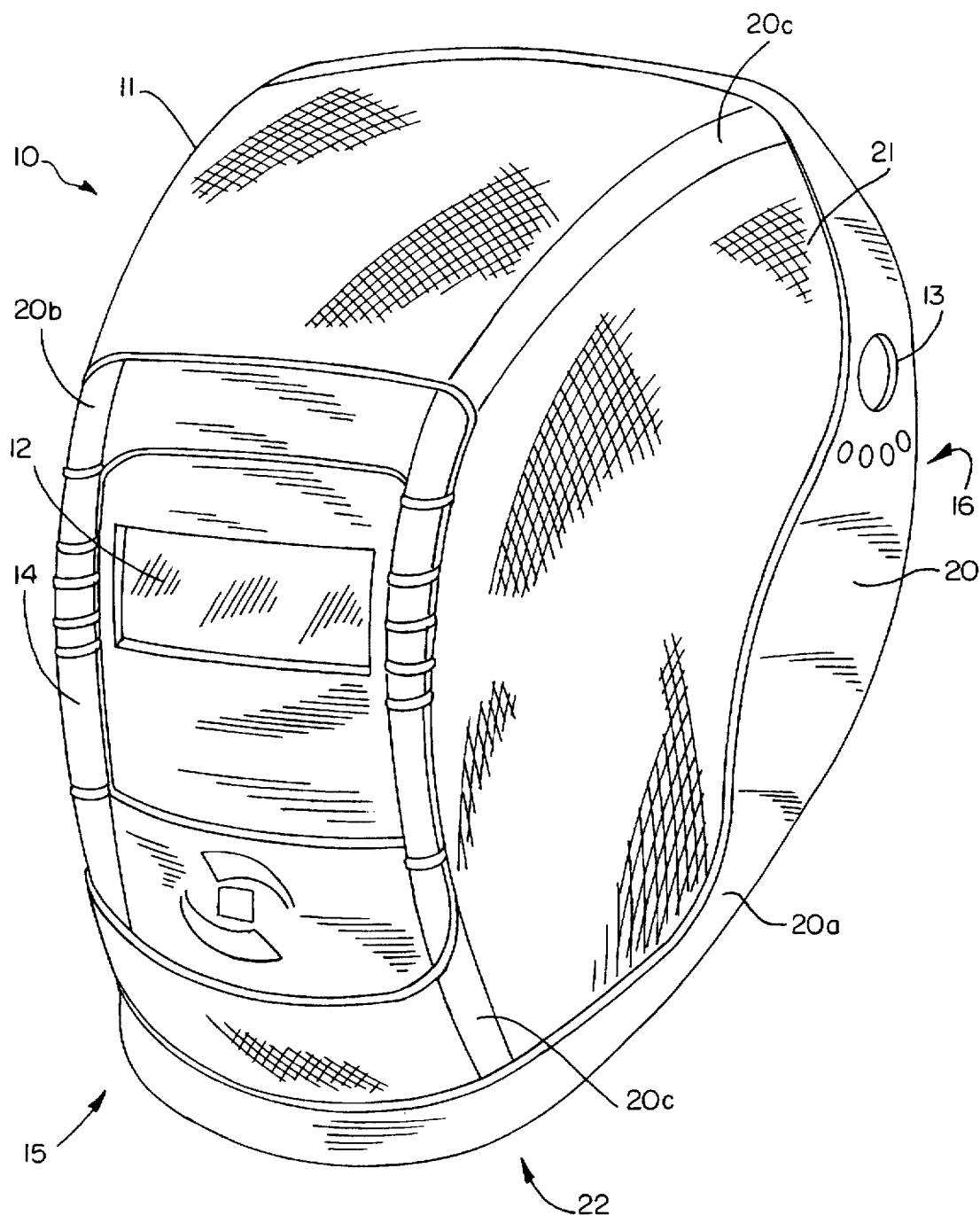
FIG. 1 is an isometric view of a welding helmet in accordance with the present invention.

Referring, now, to the drawings, wherein like reference numerals designate like parts in the several figures, and initially to FIG. 1, a welding helmet with the present invention is generally indicated at 10. The welding helmet 10 includes an outside shell 11, a viewing port 12 and viewing port filter/coverplate retainer mechanism 12, a mounting headband (not shown), and the headband pivot connection 13. The welding helmet 10 is intended to be mounted on the head of a person by placing the headband (not shown) onto the head and orienting the welding helmet to place the viewing port 12 at the front 15 of the helmet in front of the person's eyes. The back 16 of the welding helmet may be open in which the case the outside shell 11 may be pivoted about pivot holes 13a of the headband pivot connection 13 in a generally clockwise direction relative to the illustration of FIG. 1 to expose the face of the person wearing the welding helmet. Alternatively, the back 16 may be closed to provide additional isolation and/or protection for the head and face of the person wearing the welding helmet.

The outside shell 11 includes a thermoplastic frame 20 and a composite material panel 21. As is seen in FIG. 1, the thermoplastic frame 20 has two primary portions 20a, 20b. The thermoplastic frame 20 may have additional portions, too. The frame portion 20a is at the back 16 of the shell 11 and also at the bottom 22. The frame portion 20b is at the front 15 of the shell 11. The frame portion 20a includes a mechanical detail in the form of an opening for mounting the headgear or mounting headband via the pivot mechanism 13 to the shell. The frame portion 20b provides a mechanical detail for the attachment of the viewing port filter/coverplate retaining mechanism 14 to the shell 11. Additional frame members 20c in the form of web or strut-like members interconnect the frame portions 20a, 20b. Although only several of the strut members 20c are seen in FIG. 1, it will be appreciated that more or fewer than those shown may be used in the welding helmet 10 to interconnect various portions of the frame 20 and also to provide adequate structural support for the composite material 21.

Figure 2:
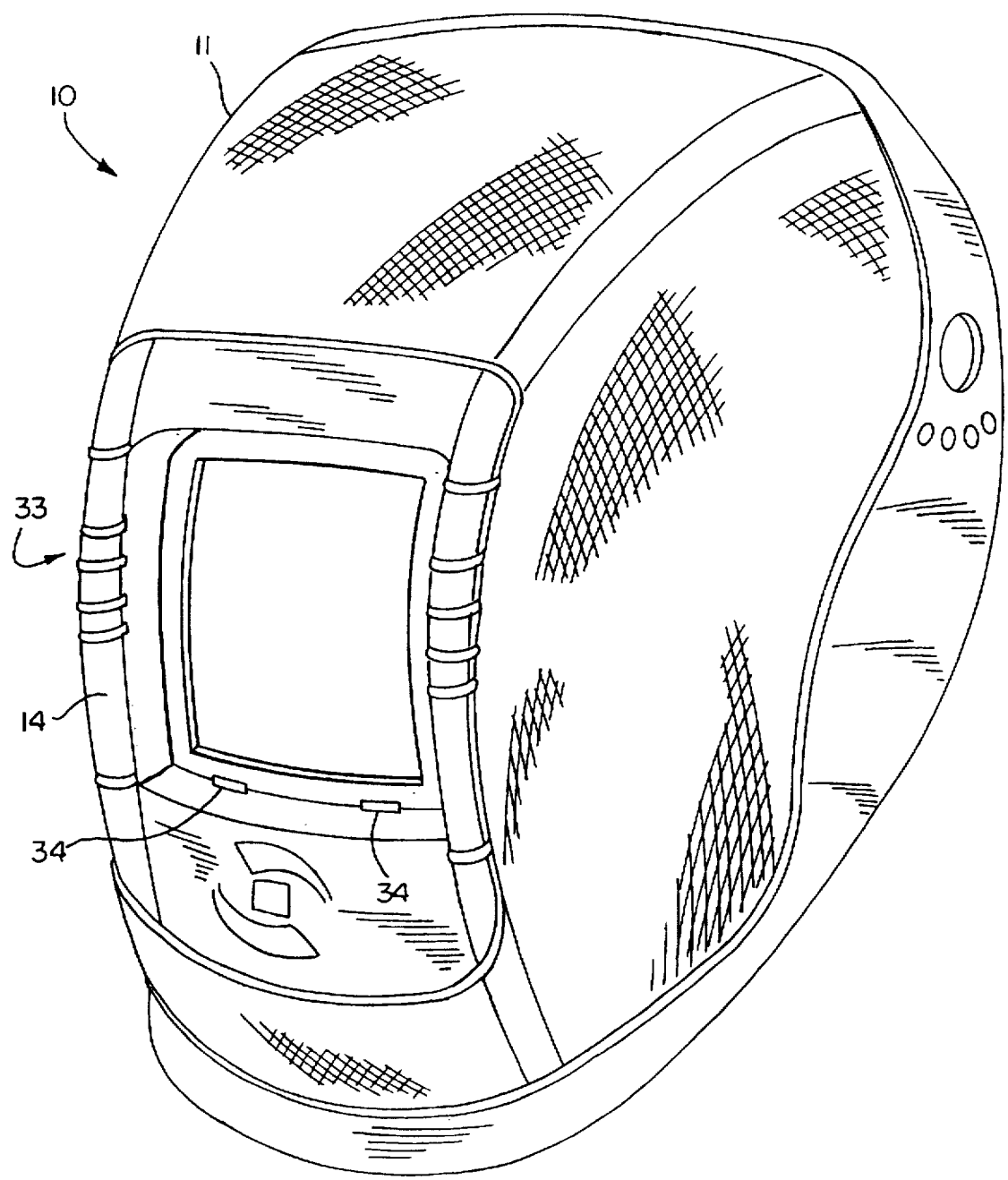
FIG. 2 is an isometric view similar to the drawing of FIG. 1 but with the filter coverplate assembly removed to show a mounting structure therefore.

As is seen in FIG. 2, the viewing port retaining mechanism 14 has been removed to expose the open area 33 where the viewing port 12 and particularly the filter/coverplate assembly 14 thereof would be installed. Hinge pivot points 34 are schematically shown for mounting the viewing port filter/coverplate assembly 14 in the area 33. Although only one pair of hinging points 34 is shown at the bottom of area 33 of the viewing port filter plate retainer mechanism 14, additional hinges (not shown) may be included at the top, and/or other mounting mechanism may be used to secure a welding lens cartridge 40 (FIG. 3), or other viewing port device in the viewing port filter plate retaining mechanism. The mounting mechanism may be specially designed for a special viewing port device or it may be somewhat universal being able to mount a variety of different types of viewing port devices in the viewing port filter plate retaining mechanism 14 of the welding helmet 10.

The viewing port may be a dark filter plate of glass or other material. The viewing port 12 may be a welding lens that automatically darkens or lightens, for example, as is described in the above-mentioned patents. Such a welding lens can be part of a cartridge assembly secured by the retainer mechanism 14 as exemplified at 40 in FIG. 3. Other types of viewing port devices also may be used.

In using the welding helmet 10, a person would place the mounting headband onto the head and would pivot the shell 11 to a desired orientation either tilted up on top of the head or tilted down in front of the face. An exemplary mounting headband or head gear is shown schematically at 13b in FIG. 7. The welding helmet 10 provides protection for the eyes of the welder from the ultraviolet, visible and infrared light emitted during welding. The shell 11 and viewing port 12 also provide a measure of protection blocking from the face fumes, heat, hot metal spatter and sparks, and possibly other debris.

The material of which the frame 20 is made preferably is a thermoplastic. One exemplary thermoplastic material is polyamide (Nylon). Other thermoplastic materials include polycarbonate, polyester, polyethylene, polyphenylene sulfide, polyimide, polyurethane, ABS, etc.

Preferably the material of which the frame 20 is made is able to be molded, more preferably injection molded, and most preferably insert molded with the preformed composite panels placed in the mold prior to the injection of the thermoplastic resin material. Insert molding is a known technique and is used, for example, in the manufacturing of electrical connectors, for example.

The material of which the composite material panel 21 is formed may be a woven fiber, such as that sold under the trademark Kevlar. Such woven fiber may be embedded in a resin matrix to form a single ply or a multiple ply (laminate) material. The composite material alternatively may be a carbon fiber material, a fiberglass material, or laminated hybrids of the various woven or non-woven materials available. The woven fiber material of which the composite material is formed preferably is provided in the form of a sheet of such material, and that sheet may be impregnated with epoxy, polyester resin, and/or resin matrix material.

To make the shell 11 of the welding helmet 10, according to an embodiment of the invention, a woven sheet of Kevlar fiber material is impregnated with epoxy or polyester resin and/or other stiffening materials. The impregnated sheet material is pressed into the desired shape and is cured using conventional techniques, such as by elevating the temperature, applying a vacuum, and/or applying pressure. This technique may be used to form a single ply or a multiple ply wall panel for the helmet. The helmet 10 may include a plurality of such wall panels, each being formed in a particular shape to cooperate with respective portions of the frame material 20 with which they are to be interconnected as an integral structure.

Alternative processes by which panels of the composite material can be fabricated also exist. One example is known as resin transfer molding (sometimes referred to as RTM) in which resin is transferred or injected into a mold where the woven fiber already has been inserted or draped to form the shape of the particular panel or object. After the resin has been cured suitably, the panel or part can be removed. The resin preferably provides suitable stiffness for the composite material. The woven fiber can be supplied in a shape that is preformed to the shape of the part intended to be made or it may be manually laid up to form the structural shape of the part and then trimmed after curing to provide the final shape of the part or the panel being made.

The frame 20 is made of thermoplastic material, as was mentioned above. In an embodiment of the invention the frame 20 is made by an insert molding technique. The insert molding technique includes placing in a mold the panels of the already formed relatively stiff composite material 21. The mold then is closed, and the panels of the composite material are held in place by the mold parts. Thermoplastic material then is injected into the mold at specified locations to form the frame 20. More particularly, preferably the mold has spaces where the thermoplastic material will flow to form the back of the frame 20a, front 20b of the frame which provides the viewing port filter plate retainer mechanism 14, and ribs 20c of the frame. The various portions of the frame 20 are directly molded to the composite material panels to form an integral structure therewith.

Figures 3, 4:
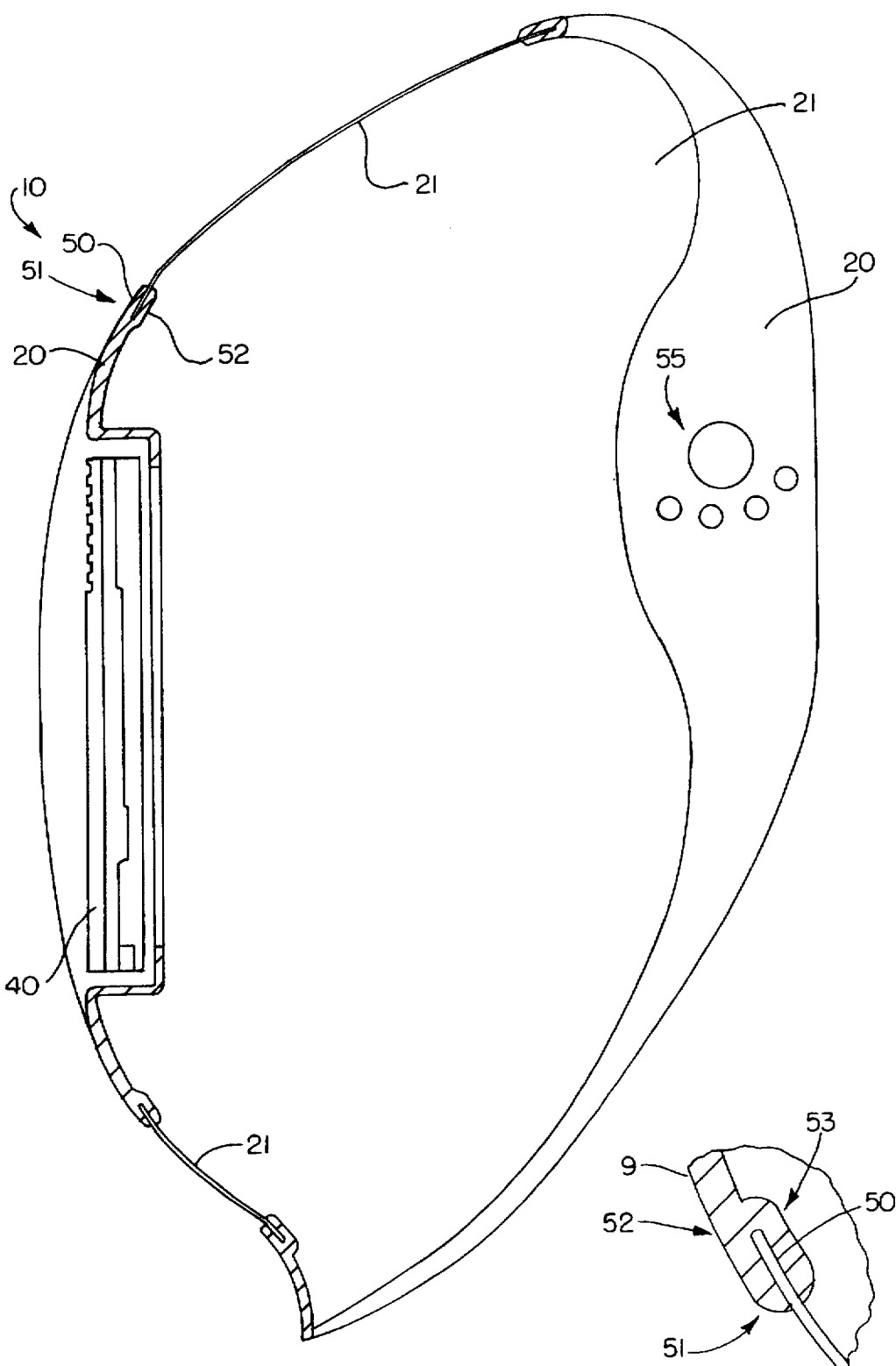
FIG. 3 is a partial side elevation section view of the welding helmet of FIG. 1.
FIG. 4 is an enlarged fragmentary section view of a junction between composite material and support material of the invention.

Turning now to FIG. 3, an elevation view of the welding helmet 10 with the front face of the helmet in section is shown. The frame 20 is molded to and attached directly to respective panels 21 of composite material at the edges 50 of those panels. The junction 51 of the panels 21 and frame 20 is a lapped type of junction as is seen in FIG. 3 and in the enlarged section view of one of the junctions in FIG. 4. The edge 50 of the panel 21 may be relatively ragged. However, the lapping frame material 52 substantially encases the ragged edge and extends along a sufficient distance of encased composite panel material shown at 53 in FIG. 4 both to provide security and integrity of the connection of junction 51.

The frame 20 preferably is sufficiently stiff to provide structural rigidity to the welding helmet 10. Additionally, the frame 20 may have various mechanical details in it for securing the viewing port retaining mechanism 14 to the frame, such as by means of the above mentioned hinge points 34, latches, screws, and rivets, etc. The frame 20 also may have a mechanical detail in the form of holes or openings 55 for attaching the mounting headband to the welding helmet.

Figure 7:
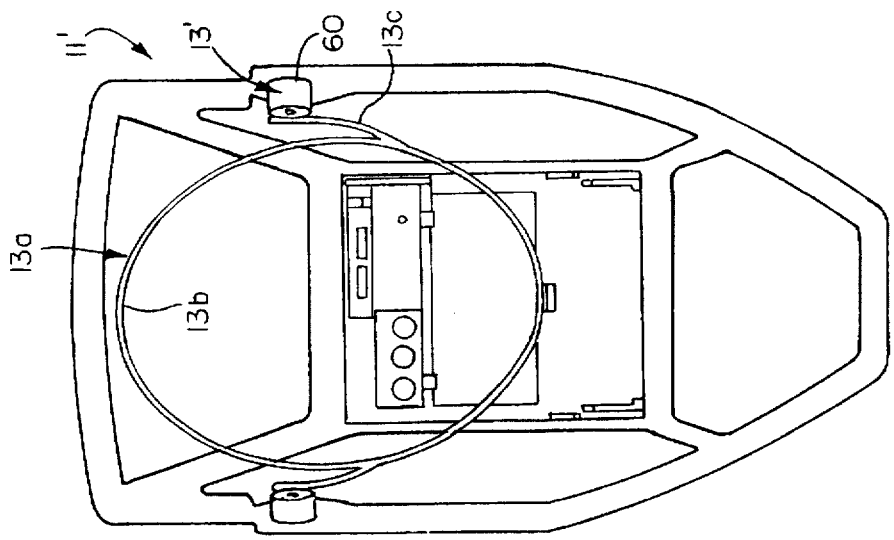
FIG. 7 is a back elevation view of the welding helmet of FIG. 5.
Figure 6:
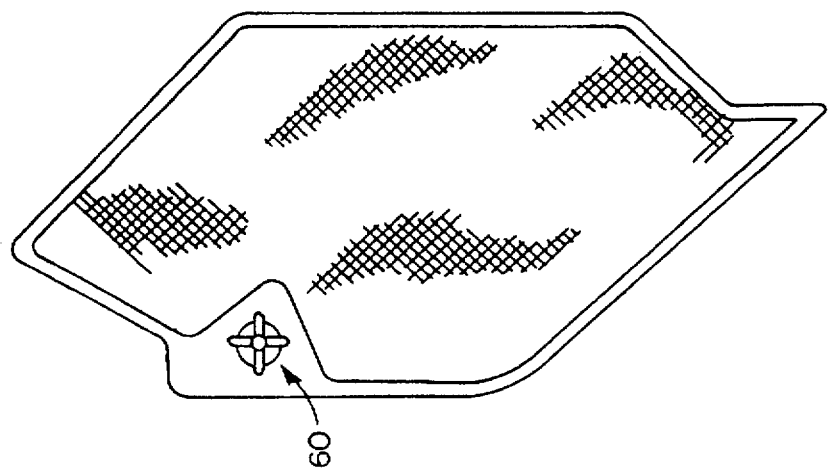
FIG. 6 is a side elevation view of the welding helmet of FIG. 5.
Figure 5:
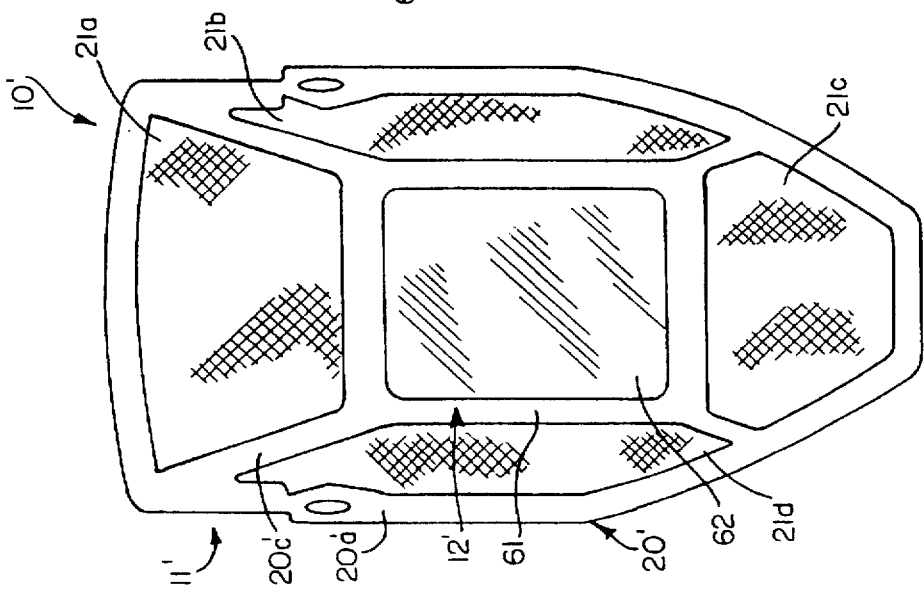
FIG. 5 is a front elevation view of another embodiment of welding helmet.

Referring to FIGS. 5–7, another embodiment of welding helmet 10' is shown. The welding helmet 10' is similar to the welding helmet 10. In FIGS. 5–7 primed reference numerals will be used to designate parts which correspond to parts in the welding helmet 10 of FIGS. 1–4 and are designated by unprimed reference numerals.

The welding helmet 10' includes an outside shell 11', a viewing port 12', head gear 13a in the form of a mounting strap 13b and a fastening strap 13c, which are connected at a pivot connection 13' to the shell 11'. A nut and bolt connection 60 seen in FIG. 7 attached the head gear 13a to the shell 11' in a conventional way.

Looking at FIG. 5, the frame 20' includes a front 61, which serves as the viewing port filter/coverplate 62 retainer. In this case it is not removable as is shown at 14 in FIGS. 1 and 2, but instead the filter and coverplate are held in place by a wire formed spring (not shown). In the welding helmet 10' an integrally formed viewing port 61 is shown with the coverplate 62 providing protection from scratching or the like is seen on the outside face thereof.

The frame 20' also includes a back frame structure 20a' and four web-like struts 20c'. Four composite panels 21a through 21d are adhered to and structurally supported by the frame 20 in the manner shown previously in FIG. 4.

The welding helmet 10' can be made using the methods described above.

Another method for making welding helmets in accordance with the present invention includes using as the composite material a material which is activated in response to the conditions that occur during the insert molding process. Therefore, the composite material may include a sheet of woven fiber material, such as Kevlar, that is impregnated or coated with a resin that melts and cures during the insert molding process and/or thereafter. For example, the sheet material is placed in the mold, and the mold is closed. The mold temperature is raised to melt the resin that is impregnating or coating the sheet material, and thermoplastic material is injected to the mold at the respective locations where the frame 20 is to be formed. After injection has taken place, mold is cooled; alternatively, the mold can be opened and cooled. During the latter processes, the thermoplastic preferably has solidified or does solidify, and the resin associated with the sheet material also cures to a relatively stiff condition.

Alternatively to the above described methods, it is possible that the composite material and the frame material can be secured together using mechanical fasteners, by adhesive bonding using an adhesive material, by heat staking, and/or by ultrasonic welding techniques. Regardless of the technique used to secure the composite material and the frame material together, it is desirable that the two are secured sufficiently well to form an integral structure or a near integral structure whereby the frame material provides structural support for the composite material.

Various mechanical features may be included in the frame material. Examples include the mounting structure for the head gear described above. Another example of a mechanical feature is the hinges or locking mechanism used to secure the viewing port 12 and subsequent filter/coverplate retainer 14 in place in the frame. Other mechanical features include devices to attach a respiration hose and to provide light filtration components to the welding helmet, shell, or other device embodying the invention.

By using composite material which is relatively light weight compared to materials previously used for welding helmets, and especially by using a frame material to provide a structural support for the composite material, the overall weight of the welding helmet 10 can be reduced compared to prior welding helmets that provided similar types of protective functions for a welder. Additionally, the welding helmet according to the invention has high temperature resistance, for example, being particularly resistant to hot metal spatter or sparks, as well as to fumes and heat generated by a welding arc due to the characteristics of the composite material and the integral connection between the composite material and the frame. Furthermore, due to the characteristics of the composite material and the cooperative structural support provided the composite material by the frame, the welding helmet has good durability being able to withstand relatively severe impacts. Thus, the overall strength of the welding helmet per volume of material required to make the welding helmet is greater than that of prior art welding helmets. By providing such strength characteristics and minimal material requirements, the weight of the welding helmet can be reduced.

INDUSTRIAL APPLICATION

It will be appreciated that the welding helmet of the invention is useful to protect welders from the hazards of bright light, heat and impacts, and the light weight characteristic of the helmet facilitates balancing on the head, provides improved comfort and fatigue. The features of the invention described may be used in various applications other than welding helmets, as is expressed above.

The embodiments of the invention claimed are, as follows:

1. A protective head gear structure comprising a composite material and a frame-like support material including a plurality of frame members forming a plurality of areas therebetween, said composite material being relatively non-transmissive of light and being disposed substantially within said areas and integrally coupled to said frame members to form an integral structure, mounting means for mounting the structure relative to the head of a person to position said composite material in protective relation to at least a portion of the head of the person, and further comprising a viewing port in the structure.

2. The structure of claim 1, further comprising a protective lens in the viewing port.

3. The structure of claim 2, said protective lens comprising a lens operable automatically to darken in response to the occurrence of a bright light condition.

4. The structure of claim 1, said frame members being integrally coupled to said composite material along substantially the entire respectively confronting portions thereof, and at least a portion of said frame members located at said viewing port to provide a mounting structure for a protective lens.

5. The structure of claim 1, said composite material forming a protective shell barrier.

6. The structure of claim 5, said composite material forming a protective barrier relative to heat, fumes, sparks, hot or molten metal occurring during welding processes.

7. The structure of claim 1, wherein said composite material comprises sheet-like material.

8. The structure of claim 1, wherein said composite material comprises sheet-like material, and said frame members are adhesively bonded to said composite material.

9. The structure of claim 1, wherein said composite material comprises sheet-like material, and said frame members are heat staked to said composite material.

10. The structure of claim 1, wherein said composite material comprises sheet-like material, and said frame members are ultrasonically welded to said composite material.

11. The structure of claim 1, further comprising light absorbing or blocking material included in said composite material.

12. The structure of claim 1, wherein said composite material comprises sheet-like material, and said support material is insert molded to said composite material.

13. A protective head gear structure comprising a composite material, a frame-like support material including a plurality of frame members forming a plurality of areas therebetween and mounting means for mounting the structure on the head of a person, said composite material being a woven sheet impregnated with a stiffening material, being relatively nontransmissive of light and being disposed substantially within said areas and integrally coupled to said frame members to form an integral structure.

14. The structure of claim 13, said stiffening material being selected from the group comprising polyester resin and epoxy.

15. The structure of claim 13, further comprising means for fastening headgear to said support material for mounting the gear on the head of a person.

16. The structure of claim 13, said composite material comprising material that has light blocking properties.

17. The structure of claim 16, said composite material comprising a material that blocks transmission of at least some of incident ultraviolet, visible and infrared light.

18. The structure of claim 13, said composite material having impact resistance and light weight characteristics, and said support material providing structural support for said composite material.

19. A protective head gear structure comprising a composite material, a frame-like support material including a plurality of frame members forming a plurality of areas therebetween, said composite material being disposed substantially within said areas and integrally coupled to said frame members to form an integral structure, mounting means for mounting the structure on the head of a person, and means for fastening a respirator connection to said support material.

20. A protective head gear structure comprising a composite material and a frame-like support material including a plurality of frame members forming a plurality of areas therebetween, said composite material being relatively non-transmissive of light and being disposed substantially within said areas and integrally coupled to said frame members to form an integral structure, said composite material comprising fiber reinforcing materials, selected from the group consisting of para-aramid fiber, carbon fiber, and fiberglass.

combined with a resin matrix material selected from the group consisting of epoxy and polyester.

21. The structure of claim 20, said support material comprising a resin from the thermoplastic family of materials.

22. The structure of claim 20, said support material being formed and cured directly in place relative to and in engagement with said composite material.

23. The structure of claim 20, said composite material having relatively rough edges, and wherein said support material fills in the rough edges to provide a relatively smooth finish.

24. The structure of claim 20, wherein said support material has a relatively smooth exterior surface at the area where said support material and composite material are connected.

25. The structure of claim 20, said composite material further comprising means for enhancing the connection between said composite material and said support material.

26. The structure of claim 20, including a mounting structure for mounting the protective head gear structure to function as a welding shield.

27. A protective head gear structure comprising a sheet-like composite material, a support material and mounting means for mounting the head gear on the head of a person, said support material comprising a frame structure adhesively bonded to said composite material to form an integral structure, said composite material further comprising means for enhancing the connection between said composite material and said support material, said means for enhancing comprising openings through said composite material, and at least some of said support material being in said openings.

28. A head gear, structure comprising a composite material and a support material, said support material being integrally coupled to said composite material to form an integral structure, wherein said composite material comprises sheet-like material having respective surfaces and said support material comprises a frame structure insert molded to said composite material, said support material forming an overlapped joint connection covering portions of both surfaces of said composite material along at least a portion of an edge of said composite material.

29. A light weight welding helmet for protecting the head of a person, comprising a plurality of relatively light weight panels of composite material which is relatively non-transmissive to light, a frame structure including a web-like structure of frame members forming a plurality of areas therebetween wherein said panels are held in relatively fixed relation and are directly molded to said frame structure, and mounting means for mounting the helmet relative to the head of a person and viewing means for permitting viewing through at least one of said panels.

30. A method of making a light weight, protective head gear formed of a plurality of panels of composite material and a plurality of interconnecting frame members surrounding the peripheries of the panels, comprising spacing the panels of such composite material in a mold of a molding machine, placing the mold material for forming the frame members in the spaces between the panels and overlapping the peripheries of the panels, and molding the frame members directly to the composite material.

31. The method of claim 30, said molding comprising raising the temperature of the composite material to activate an ingredient thereof.

32. The method of claim 30, wherein said molding includes insert molding.

33. The method of claim 30, wherein the frame members are formed of a thermoplastic material.

34. The method of claim 30, further comprising selecting said composite material from the group consisting of para-aramid fiber, woven fiber embedded in a resin matrix, carbon fiber, fiberglass, and laminated combinations of the foregoing.

35. The method of claim 30, further comprising preparing the composite material by resin transfer molding.

36. The method of claim 30, further comprising preparing the composite material by laminating sheets thereof.

37. The method of claim 30, further comprising preparing the composite material by manual lay up.

38. The method of claim 30, wherein the composite material is relatively translucent to light.

39. The method of claim 30, wherein the panels include openings along their peripheries for enhancing the connection between the panels and the frame members.

40. The method of claim 30, wherein the frame members form a smooth finish at the peripheries of the panels relative to the finish of the peripheries of the panels prior molding.

41. The method of claim 30, wherein the frame members form an overlapping joint connection covering portions of both surfaces of the panels along at least a portion of the peripheries of the panels.

* * * * *